United States Patent [19]

Welsh

[11] Patent Number: 4,515,267
[45] Date of Patent: May 7, 1985

[54] DENTAL MIXING AND EXTRUSION CAPSULE

[75] Inventor: Richard E. Welsh, Milford, Del.

[73] Assignee: Dentsply Research & Development Corp., Milford, Del.

[21] Appl. No.: 553,250

[22] Filed: Nov. 16, 1983

[51] Int. Cl.³ .............................................. B65D 25/08
[52] U.S. Cl. .................................... 206/219; 366/602; 128/272.1; 222/386
[58] Field of Search ................. 206/219; 211/DIG. 8; 366/602; 128/272.1; 222/386

[56] References Cited

U.S. PATENT DOCUMENTS

| | | |
|---|---|---|
| 1,774,258 | 8/1930 | English . |
| 3,156,369 | 11/1964 | Bowes et al. . |
| 3,344,914 | 10/1967 | Bloom et al. . |
| 3,595,439 | 7/1971 | Newby et al. ...................... 206/219 |
| 3,603,469 | 9/1971 | Magni . |
| 3,684,136 | 8/1972 | Baumann ............................. 206/219 |
| 3,831,742 | 8/1974 | Gardella et al. .................... 206/219 |
| 3,963,120 | 6/1976 | Perfect ................................ 206/219 |
| 4,136,775 | 1/1979 | Zaltsman . |
| 4,197,943 | 4/1980 | Weikel ................................ 206/219 |

FOREIGN PATENT DOCUMENTS

| | | |
|---|---|---|
| 1813233 | 7/1969 | Fed. Rep. of Germany . |
| 1939316 | 8/1969 | Fed. Rep. of Germany . |
| 2009403 | 2/1970 | Fed. Rep. of Germany . |
| 1566222 | 2/1972 | Fed. Rep. of Germany . |
| 2400970 | 1/1974 | Fed. Rep. of Germany . |

Primary Examiner—Joseph Man-Fu Moy
Attorney, Agent, or Firm—C. Hercus Just; Edward J. Hanson, Jr.

[57] ABSTRACT

A combination capsule adapted to both mix a plurality of ingredients to prepare them for use and then extrude the same through a nozzle attachable to one end of the capsule which comprises a pair of reciprocal sleeves respectively having compartments to contain different ingredients confined therein prior to the ingredients being brought into contact and the capusle being arranged to cause the ingredients to be brought together by pushing one sleeve into the other to rupture a membrane in the latter, whereby the ingredients may be agitated to mix them, followed by exchanging a cap on the outer end of the inner sleeve for an attachable nozzle and the outer end of the outer sleeve being closed by a closure having a flangible section adapted to be pushed into the sleeve and serve as a plunger to effect removal of the mixed ingredients through the nozzle.

7 Claims, 7 Drawing Figures

DENTAL MIXING AND EXTRUSION CAPSULE

BACKGROUND OF THE INVENTION

In various medical fields, including dentistry, it is necessary to mix a plurality of ingredients to form a product which is usable for various purposes. Especially in dentistry, it is common and necessary, for example, for mercury and silver powder to be mixed to form amalgum. Also, mixing of powders of various kinds which form cements and similar products is common in dentistry, to name only a few of the general type of products consumed in medical and quasi-medical techniques and practice.

One convenient means for forming mixtures of various ingredients and desired products comprises the use of capsules which usually comprise two members or more and these are provided with compartments in which the several ingredients respectively are contained until mixing of the same is desired. Then for convenience, the members or other elements of the capsule are moved suitably to cause exposure of the ingredients with each other suitably to effect mixing thereof either with or without the assistance of a pestle. The capsule is agitated in one of a number common machines a desired amount to effect mixing of the ingredients to a desired extent to form a composite product. There are a number of prior patents, both domestic and foreign, which illustrate attempts to solve the problem of initially maintaining all of the ingredients in separated relationship but the means by which they are brought into contact to effectively mix the same in machines is different. By way of example, the following patents illustrate structures of the type referred to: U.S. Pat. No. 1,774,258, English, Aug. 26, 1930; U.S. Pat. No. 3,156,369, Bowes et al, Nov. 10, 1964; U.S. Pat. No. 3,344,914, Bloom et al, Oct. 3, 1967; U.S. Pat. No. 3,603,469, Magni, Sept. 7, 1971; U.S. Pat. No. 4,136,775, Zaltsman, Jan. 30, 1979.

Present in this art also are illustrations of attempts to maintain ingredients separated but, after mixing the same, the composite product can be dispensed by the capsules being capable of having discharge means attached thereto to facilitate the delivery of the mixed ingredients to desired locations. Certain examples of this type of devices are shown in the following foreign patent publications of several types: German Patent Application No. 1,566,222, Feb. 24, 1972; German Patent Application No. 1,813,233, July 10, 1969; German Pat. No. 1,939,316, Jan. 25, 1973; German Pat. No. 2,009,403, Aug. 31, 1972; Published German Application No. 2,400,970, Mar. 20, 1975.

One area in which certain problems are solved by the present invention that have not been solved by the prior art comprises providing a capsule in which initially several compartments are formed respectively to contain separated ingredients, then effect contacting of the ingredients by operation of certain elements of the capsule, followed by the attachment of a dispensing nozzle to one end of the capsule and also provide means in the opposite end of capsule by which the mixture can be discharged forcibly through the attached nozzle head. The present invention is directed to such a combination which has been found to be a practical solution to this previously unsolved problem.

SUMMARY OF THE INVENTION

Among the principal objects of the present invention is the object to provide a capsule comprising a pair of telescoping sleeves which initially are in partially telescoped relationship, the outer sleeve having a rupturable diaphragm intermediately of the opposite ends and a closure on one end having a frangible piston-like section and defining, with said diaphragm, at said one end of the outer sleeve, a cavity to contain a first ingredient, the inner sleeve having a removable cap at the outer end and forming with said frangible diaphragm of the outer sleeve, a second cavity or compartment, and when the inner sleeve is moved telescopically inward relative to the outer sleeve, the inner end of the inner sleeve ruptures the diaphragm and thereby causes intermingling of the ingredients in the cavities to form a mixture thereof when the capsule is vibrated, and the cap for the inner sleeve also being exchangeable for a nozzle which is attachable to the outer end of the inner sleeve to permit discharge of material therethrough when a frangible piston-like section of the closure on the outer sleeve is severed to form a plunger for dispensing the mixed material when said plunger is moved inward against the mixture within the inner sleeve to effect discharge thereof through said nozzle.

Another object of the invention is to form the various components of capsule preferably by molding the same from plastic material and the diaphragm of the outer sleeve is substantially conical and pointed toward the closure on the outer sleeve, said diaphragm being of a weakened nature by providing at least one transverse line in the diaphragm which is thinner than the other portions but nevertheless providing a continuous diaphragm to prevent intermixing of the materials until the diaphragm is fractured.

A further and very important object of the present invention is to arrange the interior of the portion of the outer sleeve which is between the diaphragm and closure with a larger diameter than the opposite end portion of the outer sleeve which receives the inner end of the inner sleeve, the inner end of the inner sleeve also being arranged to fracture the diaphragm and when the inner sleeve is fully inserted into the outer sleeve, the segments of the ruptured diaphragm are fully enclosed between the inner end of the inner sleeve and the closed end of the outer sleeve, thus insuring no contamination of the mixed material with the segments of the ruptured diaphragm.

Still another object of the invention is to arrange the frangible piston-like section of the cap on the outer sleeve to have the same diameter as that of the interior of the inner sleeve and said piston-like section being connected to the closure of the outer sleeve by a weakened integral configuration which is readily fractured when said piston-like section is engaged by an external plungner of a dispensing gun or the like and is moved against said piston-like section.

A further object of the invention is to provide on the inner sleeve adjacent the end thereof to which the removable cap is attached, groove means adapted to be engaged by a holding means of a dispensing gun or the like to secure said sleeve against movement away from the aforesaid dispensing gun when the same is moving said piston-like section into the inner sleeve to act as a discharging piston.

In addition to the foregoing objects is another object to provide the inner end of the inner sleeve with a circular configuration having a substantially knife-like edge which, when inserted into the outer sleeve against the weakened portion of the piston-like section of the closure on the outer sleeve, ready severing of the piston-like section from the closure will occur. Also, at least a portion of the inner end of the piston-like section will be disposed within the inner end of the inner sleeve when the sleeves are in fully inserted relationship and thereby facilitate fracture of said weakened rim portion of the piston-like section when the latter is moved inwardly by a plunger of a dispensing gun or the like.

Still another object of the invention is to provide safety means for the capsule in the form of a lug extending from the outer wall of the inner sleeve intermediately of the opposite ends thereof and the outer sleeve having an interior longitudinal slot having a cross-section complementary to said lug and adapted to receive the same to guide movement of the inner sleeve into the outer sleeve, and said lug is adapted to engage the outer end of the outer sleeve nearest the cap on the inner sleeve when not aligned with said groove and thereby serves as a safety means to prevent unintended inward telescopic movement of the inner sleeve into the outer sleeve, but said sleeves being relatively rotatable about the axes thereof to align the lug with the outer said groove when it is desired to effect inward movement of the inner sleeve into the outer sleeve.

The aforegoing objects of the invention as well as other objects and details thereof are set forth in the following specification and illustrated in the accompanying drawings comprising a part thereof.

DETAILED DESCRIPTION OF THE PREFERRED EMBODIMENT OF THE INVENTION

Figure 1:
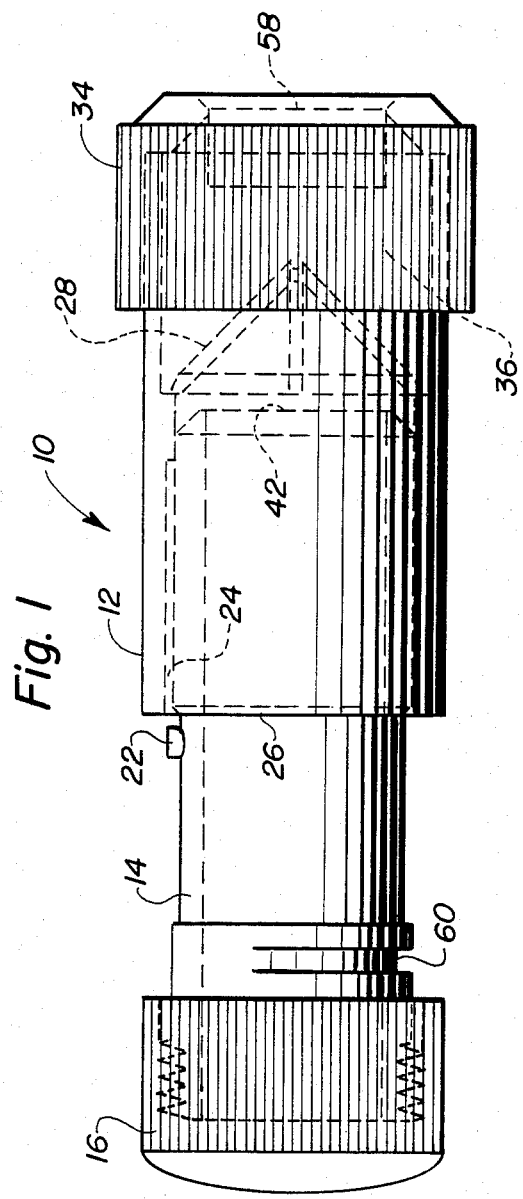
FIG. 1 is a side elevation of a capsule embodying the present invention and illustrating the initial position of the sleeves which are only partially telescoped so that the compartments thereof are separated by a frangible diaphragm.
Figure 2:
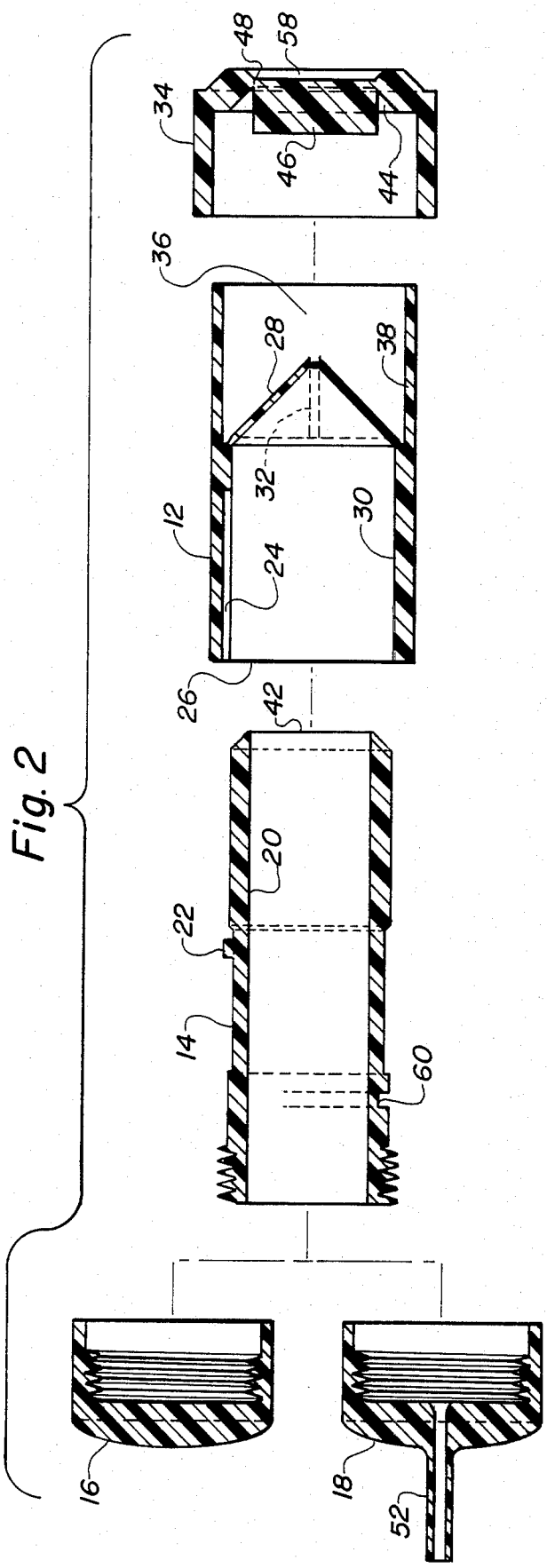
FIG. 2 is an exploded longitudinal sectional view of the components of the capsule and further includes a sectional view of a nozzle which is interchangeable with the closure cap and is threadable onto the outer end of the inner sleeve of the capsule.
Figure 3:
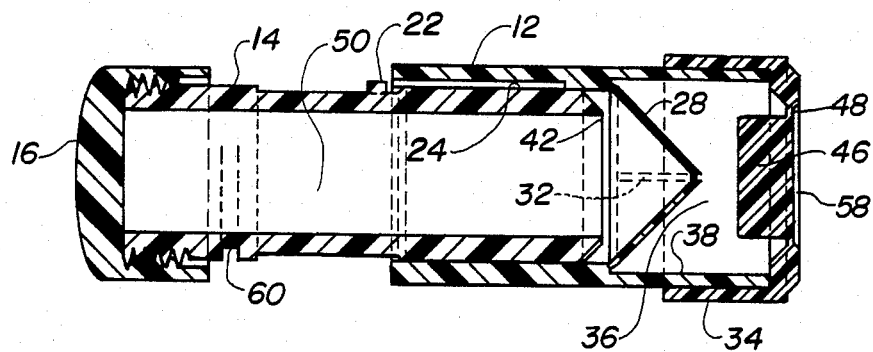
FIGS. 3–7 respectively show progressive views of the operation of the sleeves of the capsule, the same being illustrated in longitudinal sectional views described in detail hereinafter.

The preferred construction of the invention is shown especially in FIGS. 1 and 2 and comprises a capsule which includes an outer sleeve 12 and an inner sleeve 14 which are telescopically related and, in cross-section, are shown in FIGS. 3–7 in actual telescoped relationship. The outer end of inner sleeve 14 is arranged for selective connection of a cap 16 and a nozzle 18. The connection of cap 16 and nozzle 18 to sleeve 14 is shown to be of a threaded nature, but it is to be understood that other forms of connection may be used such as a friction fit, bayonet connection, or otherwise. The inner surface 20 of the inner sleeve 14 is substantially uniform, as best shown in FIG. 2.

Inner sleeve 14 is provided with a small lug 22 which is slidably received within a longitudinal interior slot 24 formed in outer sleeve 12 to provide guided telescopic movement between the respective sleeves but more particularly, to serve as a safety means which, when lug 22 out of registry with the interior slot 24, such as in the position of the lug and slot as shown in FIG. 1, the lug is capable of engaging the outer end 26 of outer sleeve 12 and thereby act as a stop to prevent accidental inward movement of the sleeve 14 relative to outer sleeve 12.

A very important feature of the invention comprises the frangible diaphragm which is of a generally pyramidal shape, preferably a conical configuration, and is integral with outer sleeve 12. The base of the diaphragm 28 is molded integrally with the outer sleeve 12 intermediately of the ends thereof and at least one weakening line 32 is formed transversely across the diaphragm to effect fracture thereof in a desired manner and preferably in the form of a pair of leaves 28' which are best shown in FIGS. 4–7, primarily in phantom. The outer end of sleeve 12 also is provided with a cap or closure 34 adapted to be cemented or otherwise fixed to the end of outer sleeve 12 which is nearest the diaphragm 28 after one of the ingredients is disposed within the cavity portion 36 between the diaphragm 28 and cap 34.

Figure 4:
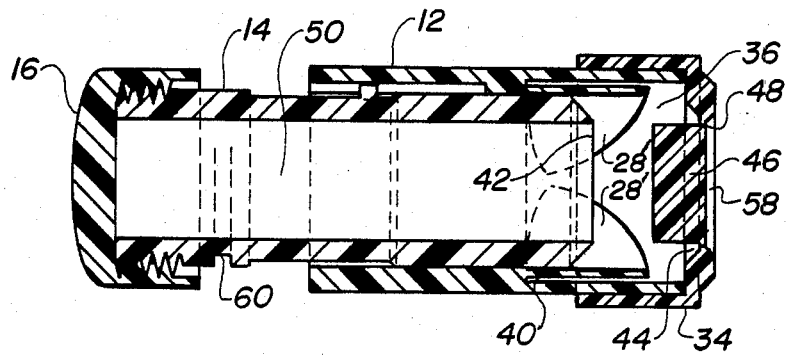
Figure 5:
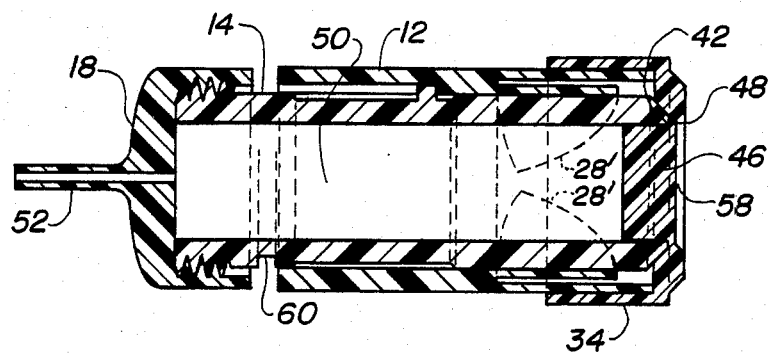

Another important feature of the invention is to provide the outer sleeve 12 with a greater inner diameter in the portion between diaphragm 28 and closure 34 to effect a clearance space 40 within outer sleeve 12 between diaphragm 28 and the capped end to accommodate the separated leaves or segments 28' of the diaphragm 28 when the diaphragm is ruptured by inward telescopic movement of the inner sleeve 14 with respect to outer sleeve 12, whereby the outer surface of inner sleeve 14 slidably moves along the separated leaves of the diaphragm, as best shown in FIG. 4, while the inner end 42 of the inner sleeve is progressively moved toward cap 34. Hence, it will be seen that the leaves of the diaphragm are still bendably connected to sleeve 12, but are completely disposed within the clearance 40 and maintained therein as the inner end 42 of sleeve 14 proceeds toward the cap 34, as shown in the progressive views illustrated in FIGS. 4–6. Such movement is continued until the beveled end 42 of inner sleeve 14 is disposed within the conical groove 44 of cap 34 which surrounds the frangible piston-like section 46 of cap 34 which is firmly affixed to outer sleeve 12, as described above.

Cap 34 also comprises a very important aspect of the present invention in that the piston-like section 46 has a diameter complementary to the inner diameter of inner sleeve 14 and is connected to the cap 34 by a circular weakened integral rim configuration 48 which is substantially circular and initially is impermeable so as to cooperate with diaphragm 28 in its initial position to form the cavity portion 36 in which one of the ingredients is disposed completely out of contact with a second compartment 50 which initially contains a second ingredient and ultimately functions as a mixing chamber.

Accordingly, when the leaves 28' of the diaphragm 28 have been been moved into the clearance 40 of outer sleeve 12, the ingredient initially in cavity 36 is intermixed with the ingredient initially in cavity 50 which, as stated above, now becomes the mixing cavity or compartment. In this stage, the completely telescoped sleeves 12 and 14 are substantially in the position shown in FIG. 5 but in which the cap 16 is still threaded onto sleeve 14. In such condition, the capsule then may be attached to or mounted within a suitable vibrating machine, or manually vibrated if desired, to effect mixing of the ingredients to a desired degree. Examples of mixing machines which are suitable comprise the subject matter of prior U.S. Pat. No. 3,749,371 to Falkenroth et al, dated July 31, 1973, and U.S. Pat. No. Des. 226,916 to Webb et al, dated May 15, 1973.

Following the mixing of the ingredients to a desired degree within the chamber or compartment 50, the cap 16 is removed and it can then be replaced by a nozzle member 18, of suitable configuration, having a discharge element or nozzle 52 in which an opening of suitable diameter is provided, depending upon the nature of the mixture to be discharged therethrough. If desired, especially to facilitate the direction of discharge material, the nozzle 52 may be at an angle of 45° or otherwise to the axis of the sleeve 14. The capsule then is introduced into a suitable dispensing gun or mechanism 54, one example of which is shown in phantom in FIG. 6, which is provided with a plunger 56, operated by any suitable means, not shown. To facilitate the engagement of the outer end of plunger 56 with the piston-like section 46 of cap 34, the latter is provided with a seat area 58. To prevent the movement of the assembled sleeves and especially inner sleeve 14 away from the plunger 56, it will seen that sleeve 14 is provided with a substantially U-shaped groove 60 which is adapted to be engaged by a suitable yoke 62, or other means shown on the gun or mechanism 54 and illustrated in FIG. 6 in exemplary manner.

It should be understood when the assembled capsule is mounted within the gun or mechanism 54, the nozzle 18 will have been substituted for the cap 16 and by operating the plunger 56, extrusion of the mixed material through the opening of the discharge element 52 takes place. As shown, for example, in FIG. 7, the piston-like section 46 is capable of being moved to the full extent of the mixing cavity within the inner sleeve 14 and thereby it is possible to effect removal of substantially all of the mixed material from the compartment 50, except possibly for that which remains in the opening of the discharge element 52.

Figure 6:
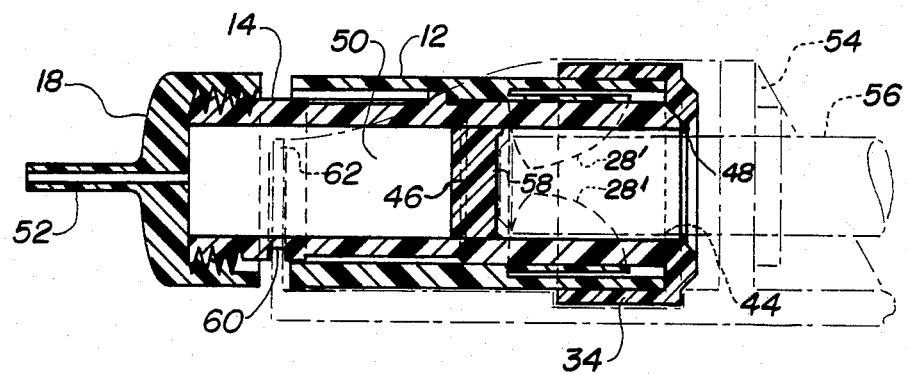
Figure 7:
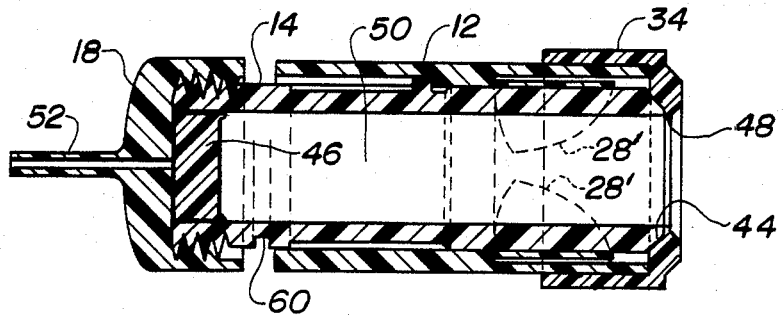

It also will be seen that, preferably, when the inner sleeve 14 has been inserted to its fullest extent within outer sleeve 12, the beveled inner end 42 of sleeve 14 is received within conical groove 44 of cap 34, as shown in FIGS. 6 and 7, and this arrangement provides firm support for the weakened integral configuration 48 and facilitates the shearing or separation of the frangible piston-like section 46 from the cap 34 and, due to the outer diameter of the section 46 being closely complementary to the inner diameter of the inner sleeve 14, effective piston function of the section 46 is assured for removal of the mixed material from the compartment 50 through the discharge element 52.

It thus will be seen that the present invention provides an actual combination mixing and extrusion capsule which fulfills a need long existing in the mixing and extrusion art and especially that section of the art pertaining to medical and quasi-medical fields, and particularly including dentistry.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown therein.

It is claimed:

1. A combination dental mixing and extrusion capsule including a pair of slidably telescoping sleeves, initially in partial telescopic relationship, the outer sleeve having a frangible diaphragm intermediately of its ends and a closure on one end having an integral frangible piston-like section and defining with said diaphragm a compartment for a first ingredient, the inner sleeve having a removable closure at the outer end defining with said frangible diaphragm of the outer sleeve another compartment for a second ingredient, the inner sleeve being movable telescopically inward to cause the inner end thereof to fracture the diaphragm and cause intermingling of the first and second ingredients to effect mixing thereof when the capsule is vibrated, and a nozzle optionally exchangeable for the removable closure on the inner sleeve to permit discharge of mixed material therethrough when said frangible piston-like section of the closure on the outer sleeve is severed by a plunger and is moved inward piston-like against the mixed material in the compartment of the inner sleeve, said frangible piston-like section having a diameter complementary to the inner diameter of said inner sleeve and also has a rim portion connected to the closure on the outer sleeve by a weakened integral configuration readily fractured when said piston-like section is engaged by an external plunger of a dispensing gun or the like and is moved against said piston-like section.

2. The capsule according to claim 1 in which the inner end of said inner sleeve is bevelled and said frangible diaphragm is substantially conical and pointed toward the closure of said outer sleeve and said diaphragm being weakened along at least one separative line to cause separation of the diaphragm when engaged by the bevelled end of said inner sleeve while the separated segments remain at least partially attached to the inner portion of the outer sleeve to prevent intermingling of the fractured diaphragm with the material being mixed.

3. The capsule according to claim 1 further characterized by said inner sleeve having means adjacent the end thereof to which the removable cap is attached adapted to be engaged by holding means of a dispensing gun or the like to secure said sleeve against movement away from the aforesaid plunger of a dispensing gun when moving said piston-like section into said inner sleeve.

4. The capsule according to claim 1 further characterized by the inner end of said inner sleeve being beveled and when fully inserted into said outer sleeve said beveled end abuts the interior portion of the closure on the outer sleeve surrounding the weakened rim portion of said piston-like section of said closure on said outer sleeve and also telescopically receives at least the innermost portion of the inner end of said piston-like section to thereby facilitate fracture of said weakened rim portion when said piston-like section is engaged by a plunger of a dispensing gun or the like.

5. The capsule according to claim 1 in which said inner sleeve has a lug on the outer wall thereof intermediately of the opposite ends thereof and the outer sleeve has an interior longitudinal groove having a cross-section complementary to said lug and adapted to receive said lug to guide movement of the inner sleeve into said outer sleeve when the lug is aligned with said groove, and said lug being adapted to engage the end of the outer sleeve nearest the cap on the inner sleeve when not aligned with said groove and thereby serve as a safety means to prevent unintended inward telescopic movement of the inner sleeve into the outer sleeve.

6. A combination dental mixing and extrusion capsule comprising in combination, a pair of slidably telescoping sleeves initially in partial telescopic relationship, the outer sleeve having a frangible diaphragm intermediately of its ends and a closure on one end, said diaphragm being engageable by the inner end of said inner sleeve to rupture said diaphragm when said inner sleeve is moved axially toward said diaphragm, and a closure on the outer end of said outer sleeve operable to define with said diaphragm a compartment for a first ingredient separated from but adapted when said diaphragm has been ruptured to be mixed with a second ingredient stored in said inner sleeve, said closure having a frangible piston-like section of a diameter complementary to the inner diameter of said inner sleeve and operable when separated from said closure to comprise a piston operable to eject mixed material from the outer end of said inner sleeve, and a seat provided on the outer end of said piston-like section engageable by the end of a plunger of external means to effect ejecting movement of said section.

7. The capsule according to claim 6 further characterized by said piston-like section being connected to said closure by an integral weakened circular rim portion surrounding said piston-like section, and the inner end of said inner sleeve when fully inserted into said outer sleeve abutting the inner portion of said closure adjacent said piston-like section to facilitate separation of said piston-like section from said closure when said section is engaged by external means to separate the same from said closure and thereby permit said section to function as a piston as aforesaid.

* * * * *